United States Patent
Jin et al.

(10) Patent No.: US 9,151,511 B2
(45) Date of Patent: Oct. 6, 2015

(54) METHOD FOR CONTROLLING AIR CONDITIONER AND ENVIRONMENTAL TESTER

(75) Inventors: Yasuharu Jin, Osaka (JP); Ryuichi Kaji, Osaka (JP)

(73) Assignee: NAGANO SCIENCE CO., LTD., Osaka (JP)

( * ) Notice: Subject to any disclaimer, the term of this patent is extended or adjusted under 35 U.S.C. 154(b) by 590 days.

(21) Appl. No.: 13/126,350

(22) PCT Filed: Oct. 28, 2009

(86) PCT No.: PCT/JP2009/005707
§ 371 (c)(1),
(2), (4) Date: Apr. 27, 2011

(87) PCT Pub. No.: WO2010/050205
PCT Pub. Date: May 6, 2010

(65) Prior Publication Data
US 2011/0213501 A1    Sep. 1, 2011

(30) Foreign Application Priority Data
Oct. 28, 2008    (JP) .................................. 2008-276623

(51) Int. Cl.
*F24F 11/00* (2006.01)
*G01N 17/00* (2006.01)

(52) U.S. Cl.
CPC ............. *F24F 11/006* (2013.01); *F24F 11/001* (2013.01); *G01N 17/002* (2013.01); *F24F 2011/0035* (2013.01)

(58) Field of Classification Search
None
See application file for complete search history.

(56) References Cited

U.S. PATENT DOCUMENTS

| | | | | | |
|---|---|---|---|---|---|
| 5,325,678 | A | * | 7/1994 | Borah et al. | .................... 62/126 |
| 5,465,588 | A | * | 11/1995 | McCahill et al. | ............... 62/127 |
| 5,588,589 | A | | 12/1996 | Ishihara et al. | |
| 5,682,329 | A | * | 10/1997 | Seem et al. | ................... 700/276 |

(Continued)

FOREIGN PATENT DOCUMENTS

| | | |
|---|---|---|
| CN | 1129308 | 8/1996 |
| CN | 1643304 | 7/2005 |

(Continued)

OTHER PUBLICATIONS

Minsung Kim, Seok Ho Yoon, Piotr A. Domanski, W. Vance Payne, Design of a steady-state detector for fault detection and diagnosis of a residential air conditioner, International Journal of Refrigeration, vol. 31, Issue 5, Aug. 2008, pp. 790-799.*

(Continued)

*Primary Examiner* — Darrin Dunn
*Assistant Examiner* — Christopher E Everett
(74) *Attorney, Agent, or Firm* — Young & Thompson

(57) ABSTRACT

An example control method is a method for controlling an air conditioner to turn a state in closed space to a predetermined target state. The control method includes: setting a target value for controlling a physical quantity; measuring the physical quantity at different positions in the closed space, and calculating a moving average of measurements of the physical quantity measured at each of the different positions; and controlling the air conditioner in such a manner that a median between the maximum value and the minimum value of the plurality of calculated moving averages is the target value.

9 Claims, 9 Drawing Sheets

(56) References Cited

U.S. PATENT DOCUMENTS

| | | | | |
|---|---|---|---|---|
| 5,792,427 | A * | 8/1998 | Hugh et al. | 422/109 |
| 5,892,367 | A * | 4/1999 | Magee et al. | 324/750.14 |
| 6,178,757 | B1 * | 1/2001 | Sitte et al. | 62/126 |
| 6,703,852 | B1 * | 3/2004 | Feltner | 324/750.03 |
| 7,479,795 | B2 * | 1/2009 | Hayashi et al. | 324/750.09 |
| 8,260,474 | B2 * | 9/2012 | Ahuja et al. | 700/300 |
| 2002/0011072 | A1 * | 1/2002 | Hiraoka et al. | 62/126 |
| 2003/0065409 | A1 * | 4/2003 | Raeth et al. | 700/31 |
| 2006/0095157 | A1 * | 5/2006 | Raterman | 700/231 |
| 2006/0244472 | A1 * | 11/2006 | Hayashi et al. | 324/760 |
| 2008/0135634 | A1 * | 6/2008 | Murakami et al. | 236/51 |
| 2009/0281667 | A1 * | 11/2009 | Masui et al. | 700/276 |

FOREIGN PATENT DOCUMENTS

| | | |
|---|---|---|
| CN | 1727792 | 2/2006 |
| EP | 1496316 | 1/2005 |
| JP | 07-140061 | 6/1995 |
| JP | 10-073301 | 3/1998 |
| JP | 2002-005489 | 1/2002 |
| JP | 2003-021382 | 1/2003 |
| JP | 2005-172304 | 6/2005 |
| JP | 2006-096306 | 4/2006 |
| JP | 2007-057231 | 3/2007 |
| JP | 2007-085569 | 4/2007 |
| JP | 2007-225496 | 9/2007 |
| JP | 2008-275345 | 11/2008 |
| JP | 2009-103347 | 5/2009 |
| JP | 2009-228926 | 10/2009 |
| JP | 2010-139119 | 6/2010 |
| WO | WO 2008/007433 * | 1/2008 |

OTHER PUBLICATIONS

International Search Report, PCT/JP2009/005707, Feb. 2, 2010.
Sekikawa, "Adjustment temperature / the adjustment humidity of environmental examination device", The point of the temperature / humidity control sensor. Test vol. 7, p. 20.

* cited by examiner

METHOD FOR CONTROLLING AIR CONDITIONER AND ENVIRONMENTAL TESTER

TECHNICAL FIELD

The disclosed technology can be applied to environmental testers, such as thermostat chambers and thermostat-humidistat chambers, and relates to an air conditioner which can turn a state in closed space to a predetermined target state, and a method for controlling the air conditioner.

BACKGROUND ART

Environmental testers, such as thermostat chambers and thermostat-humidistat chambers used for material tests, which can stably keep physical quantities, such as temperature, humidity, etc., in a test chamber as closed space to predetermined target values have been known (see, e.g., Patent Document 1). In such an environmental tester, a temperature sensor and a humidity sensor are provided in the test chamber surrounded by adiabatic walls, and an air conditioner including a refrigerator, a humidifier, and a heater is controlled based on the values measured by the sensors. Thus, air is circulated between the test chamber and the air conditioner, and the temperature and the humidity in the test chamber are kept to target temperature and target humidity, respectively.

CITATION LIST

Patent Document

[Patent Document 1] Japanese Patent Publication No. H07-140061

SUMMARY OF THE INVENTION

Technical Problem

In such environmental testers, the temperature sensor and the humidity sensor for measuring the physical quantities used to control the air conditioner are generally arranged near an air outlet through which the conditioned air is supplied. This is because the temperature and the humidity measured near the outlet of the conditioned air can change quickly in response to the control of the air conditioner with a small lag, thereby allowing stable control of the air conditioner.

The inventors of the present invention have found that the temperature and the humidity near the sensor are merely adjusted to the target temperature and the target humidity when only a single sensor for measuring the temperature and the humidity is provided near the air outlet, and that the temperature and the humidity are not always adjusted to the target temperature and humidity in the entire part of the test chamber. For example, ranges of spatial distributions of the temperature and the humidity in the test chamber (a difference between the maximum value and the minimum value) are deviated from the target temperature and humidity. As a result, the temperature and the humidity of a particular part in the test chamber may deviate from the allowable range around the target temperature, and the allowable range around the target humidity.

Thus, the inventors of the present invention have studied arranging a sensor for measuring the temperature and the humidity at the center of the test chamber, for example, to control the air conditioner in such a manner that the temperature and the humidity at the center of the test chamber are the target temperature and the target humidity, respectively. This configuration can reduce the deviation of the ranges of the distributions of the temperature and the humidity from the target temperature and humidity, and the distributions of the temperature and the humidity are likely to be kept within the allowable ranges. However, since a distance between the sensor arranged at the center of the test chamber and the control system of the air conditioner is increased, changes in temperature and humidity measured by the sensor are delayed in time from the control of the air conditioner. As a result, hunting of the control system is likely to occur.

SOLUTION TO THE PROBLEM

The disclosed technology has been achieved in view of the foregoing. An object of the disclosed technology is to stably control the air conditioner, and reliably keep the distribution of the physical quantity representing the state in the closed space within the allowable range.

To achieve the object, the inventors of the present invention have focused on measurement of the physical quantities at different positions in the closed space, and calculation of moving averages of the physical quantities. Then, the air conditioner is controlled in such a manner that a median between the maximum value and the minimum value of the plurality of calculated moving averages is target physical quantity.

Specifically, the disclosed method is a method for controlling an air conditioner which conditions air sucked from closed space through an air inlet, and then discharges the conditioned air to the closed space through an air outlet, thereby controlling a state in the closed space to a predetermined target state.

The control method includes: setting a target value for controlling a physical quantity representing the state of the closed space; measuring the physical quantity over time at a plurality of different positions in the closed space; calculating a moving average of measurements of the physical quantity measured at each of the different positions; and controlling the air conditioner in such a manner that a median between the maximum value and the minimum value of the plurality of calculated moving averages is the target value.

Advantages of the Invention

According to the disclosed technology, the air conditioner is feedback-controlled based on the moving averages of the measurements of the physical quantity obtained at the different positions in the closed space. This can stably control the air conditioner, and can reduce the deviation of the range of distribution of the physical quantity in the closed space from the target value. This is advantageous in reliably keeping the distribution of the physical quantity in the closed space within the allowable range.

DESCRIPTION OF EMBODIMENTS

Figure 1:
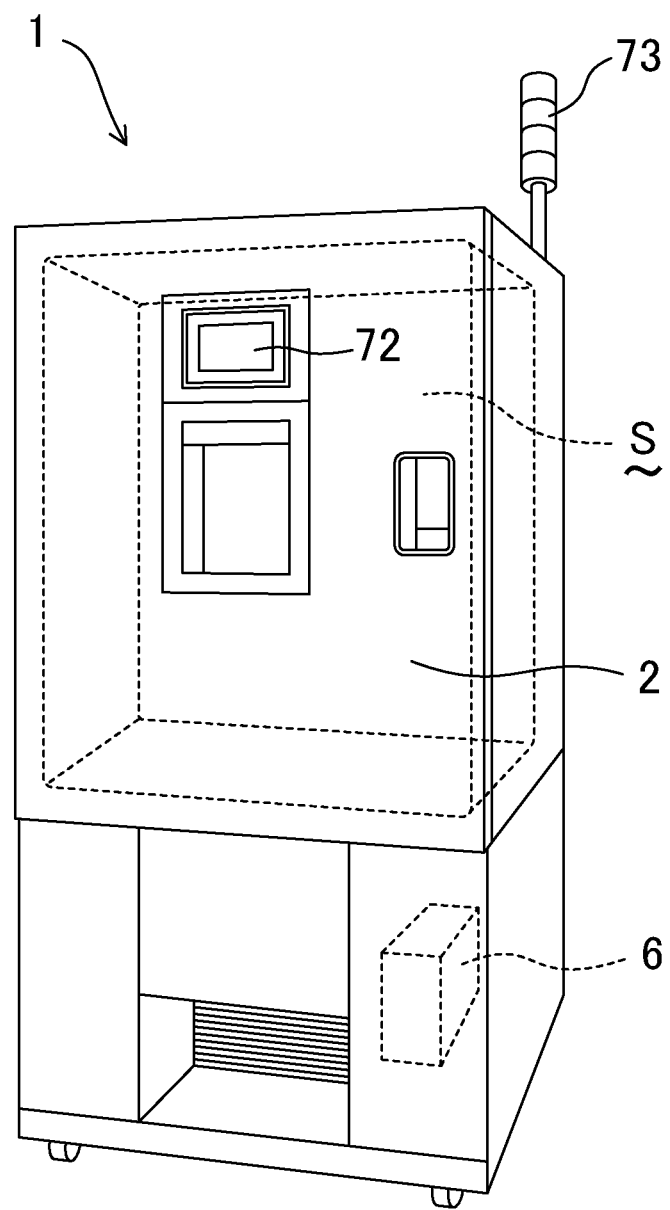
FIG. 1 is a perspective view illustrating an example of appearance of a thermostat-humidistat chamber.

The disclosed method is a method for controlling an air conditioner which conditions air sucked from closed space through an air inlet, and then discharges the conditioned air to the closed space through an air outlet is controlled, thereby controlling a state in the closed state to a predetermined target state.

The control method includes: setting a target value for controlling a physical quantity representing the state of the closed space; measuring the physical quantity over time at a plurality of different positions in the closed space; calculating a moving average of measurements of the physical quantity measured at each of the different positions; and controlling the air conditioner in such a manner that a median between the maximum value and the minimum value of the plurality of calculated moving averages is the target value.

With this configuration, the physical quantity is measured over time at each of the different positions in the closed space. The measurements of the physical quantity are measurements of the physical quantity obtained in the closed space, which precisely indicate the state in the closed space.

Then, the moving average of the measurements of the physical quantity measured at each of the different positions is calculated, and the air conditioner is controlled in such a manner that the median between the maximum value and the minimum value of the plurality of calculated moving averages is the target value.

When the air conditioner is controlled in this way using the moving averages of the measurements, hunting of the control can be prevented, and the air conditioner can stably be controlled because the parameter for such control shows gentle temporal variation.

It is advantageous to control the air conditioner based on the median of the range of distribution of the measurements of the physical quantity obtained at the plurality of different positions in the closed space, because positive and negative ranges of the distribution of the physical quantity in the closed space relative to the target value become equal. This can reduce deviation of the range of the distribution of the physical quantity in the closed space from the target value, thereby reliably keeping the range of the distribution of the physical quantity within the allowable range.

The control method described above may include: second measuring the physical quantity of the air discharged through the air outlet, or sucked through the air inlet over time; second calculating a moving average of measurements of the physical quantity measured in the second measuring; and second controlling the air conditioner in such a manner that the moving average of the measurements of the physical quantity calculated in the second calculating is the target value.

The second controlling may be performed during a transient period in which the target value is initialized or reset.

When the air conditioner is controlled based on the moving average of the measurements obtained in the closed space as described above, the parameter for such control only includes information representing a relatively long-term trend. Therefore, during the transient period in which the target value is changed, the control may become unstable.

During the transient period in which the target value is initialized or reset, the physical quantity of the air discharged from the air outlet, or sucked through the air inlet is measured over time, and the air conditioner is controlled based on the moving average of the measurements of the physical quantity. This can stably control the air conditioner, and can change the state in the closed space quickly to the target state.

The control method described above may further include: optimizing an angle of a blade which is attached to the air outlet to change a discharge direction of the conditioned air, wherein the optimizing includes: temporarily determining the angle of the blade to a predetermined angle; measuring the physical quantity at different positions in the closed space; calculating a moving average of measurements of the physical quantity measured at each of the different positions; storing a difference between the maximum value and the minimum value of the plurality of calculated moving averages; repeating the measuring, the calculating, and the storing, while changing the temporarily determined angle of the blade; and setting the angle of the blade to an optimum angle at which the difference between the maximum value and the minimum value of the moving averages is reduced as much as possible based on the stored information.

Specifically, when the range of the distribution of the physical quantity in the closed space is too wide, the range of distribution of the physical quantity may deviate from the allowable range even when the positive and negative ranges of the distribution of the physical quantity relative to the target physical quantity are equal as described above.

Thus, the angle of the blade is adjusted to reduce the range of the distribution of the physical quantity in the closed space as much as possible. In combination with the equalizing of the positive and negative ranges of the distribution of the physical quantity relative to the target value, the adjustment of the blade angle can more reliably prevent the deviation of the range of the distribution of the physical quantity from the allowable range.

Another method for controlling the air conditioner includes: setting a target value for controlling a physical quantity representing the state of the closed space; first measuring the physical quantity of the air discharged through the air outlet, or sucked through the air inlet over time; second measuring the physical quantity over time at least one position in the closed space which is not near the air outlet and the air inlet; first calculating a moving average of measurements of the physical quantity obtained at a specific position, which is the air outlet or the air inlet, in the first measuring; second calculating a moving average of measurements of the physical quantity in the closed space obtained in the second measuring; calculating a correction amount by subtracting the moving average of the measurements of the physical quantity obtained at the specific position from the moving average of the measurements of the physical quantity obtained in the closed space; adding the calculated correction amount to the physical quantity measured in the first measuring to calculate a physical quantity for control, and controlling the air conditioner in such a manner that the physical quantity for control is the target value.

With this configuration, the physical quantity of the air discharged through the air outlet, or sucked through the air inlet is measured over time in the first measuring. The air outlet and the air inlet are provided near the air conditioner.

Thus, the physical quantity measured at this position can change quickly in response to the control of the air conditioner with a short lag.

In the second measuring, the physical quantity is measured over time at least one position in the closed space which is not near the air outlet and the air inlet. The measurements of the physical quantity obtained at this position are the measurements of the physical quantity obtained in the closed space, which indicate the state in the closed space more precisely.

The moving average of the measurements of the physical quantity obtained at the specific position in the first measuring is calculated, and the moving average of the measurements of the physical quantity in the closed space obtained in the second measuring step is calculated. Then, the correction amount is calculated by subtracting the moving average of the measurements of the physical quantity obtained at the specific position from the moving average of the measurements of the physical quantity obtained in the closed space. Then, the calculated correction amount is added to the physical quantity measured in the first measuring to obtain a physical quantity for control. Since the correction amount is based on the moving averages, its temporal variation is significantly slower than the measured temporal variation of the physical quantity. Thus, measuring the physical quantity in the vicinity of the air conditioner allows the physical quantity for control to contain a temporal variation component which is approximately the same as that of the physical quantity having a small lag for controlling the air conditioner. The physical quantity for control contains information of the physical quantity measured in the closed space (the moving average of the physical quantities in the space).

Specifically, by adding the correction amount to the physical quantity measured in the first measuring, the moving average of the measurements of the physical quantity obtained at the specific position is subtracted from the measurement of the physical quantity. As a result, the temporal variation component of the physical quantity measured near the air conditioner is obtained. By adding the correction amount to the physical quantity measured in the first measuring, the moving average of the measurements of the physical quantity in the space measured in the second measuring is obtained. Thus, the air conditioner is feedback-controlled in such a manner that the moving average of the physical quantity in the space is the target value.

This allows stable control of the air conditioner, and reduces the deviation of the range of the distribution of the physical quantity in the closed space from the target value, thereby keeping the range of the distribution of the physical quantity within the allowable range.

The second measuring may be performed to obtain the measurements of the physical quantity at the plurality of different positions in the closed space. The calculating the moving average of the measurements of the physical quantity in the closed space may be performed to calculate the moving average of the measurements of the physical quantity obtained at each of the different positions. The calculating the correction amount may be performed by subtracting the moving average of the measurements of the physical quantity obtained at the specific position from a median between the maximum value and the minimum value of the plurality of calculated moving averages.

With this configuration, the air conditioner is feedback-controlled in such a manner that the median of the range of the distribution of the physical quantity in the closed space is the target value, and the positive and negative ranges of the distribution of the physical quantities relative to the target value can become equal. As a result, the range of distribution of the physical quantity in the closed space can more reliably be kept within the allowable range. This can keep the range of the distribution of the physical quantity in the closed space within the allowable range with more reliability.

An example air conditioner includes: an air conditioning part which conditions air sucked from closed space through an air inlet, and discharges the conditioned air to the closed space through an air outlet; a sensor for measuring a physical quantity at different positions in the closed space; and a controller for controlling the air conditioning part based on measurements of the sensor in such a manner that a state in the closed space is a predetermined target state, wherein the controller includes: a setting section for setting a target value for controlling the physical quantity based on an input signal; a calculating section for calculating a moving average of the measurements of the physical quantity measured at each of the different positions; and a controlling section for controlling the air conditioning part in such a manner that a median between the maximum value and the minimum value of the plurality of calculated moving averages is the target value.

With this configuration, as described above, the air conditioning part is feedback-controlled based on the moving averages of the measurements of the physical quantity obtained at the different positions in the closed space. This allows stable control of the air conditioning part, and can reduce the deviation of the range of the distribution of the physical quantity in the closed space from the target value, thereby keeping the range of the distribution of the physical quantity within the allowable range.

An example environmental tester includes: a test chamber in which a specimen is placed; an air conditioner which conditions air sucked from the test chamber through an air inlet, and discharges the conditioned air to the test chamber through an air outlet; a sensor for measuring a physical quantity at different positions in the test chamber; and a controller for controlling the air conditioner based on measurements of the sensor in such a manner that a state in the test chamber is a predetermined target state, wherein the controller includes: a setting section for setting a target value for controlling the physical quantity based on an input signal; a calculating section for calculating a moving average of measurements of the physical quantity measured at each of the different positions; and a controlling section for controlling the air conditioner in such a manner that a median between the maximum value and the minimum value of the plurality of calculated moving averages is the target value.

Referring to the drawings, the example air conditioner, and a method for controlling the same will be described below. The following description is provided merely for the illustrative purpose, and does not limit the applications and uses of the disclosed technology.

(First Embodiment)

Figure 2:
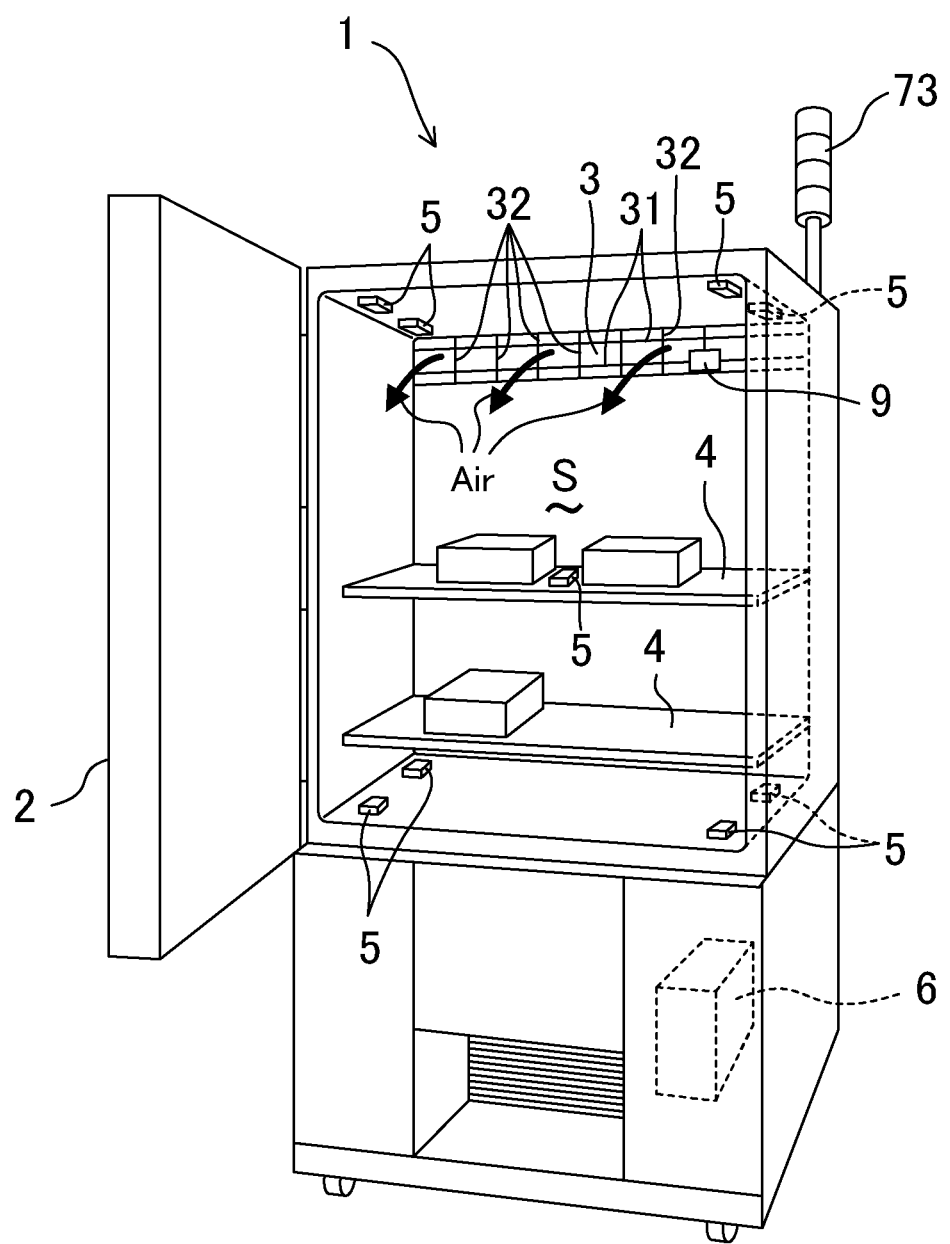
FIG. 2 is a perspective view illustrating an example of the inside of the thermostat-humidistat chamber.

FIGS. 1 and 2 show a thermostat-humidistat chamber 1 as an example environmental tester. The thermostat-humidistat chamber 1 is used for stability tests of pharmaceuticals, for example. For this reason, temperature and humidity in a test chamber S are stably kept within the predetermined ranges, respectively.

As shown in FIG. 2, an air outlet 3 is formed in an uppermost portion of a back wall of the test chamber S, through which conditioned air of adjusted temperature and humidity is discharged to the test chamber S from an air conditioner 8 including a refrigerator, a humidifier, a heater, etc. (see FIG. 3). Although not shown, an air inlet is formed in a lowermost portion of the back wall of the test chamber S, through which the air is supplied to the air conditioner 8. Thus, in the thermostat-humidistat chamber 1, the air is circulated between the test chamber S and the air conditioner 8, thereby stably keeping the temperature and the humidity in the test chamber S within the predetermined ranges, respectively.

A plurality of blades 31 which extend in the horizontal direction, and are capable of moving in the vertical direction to change an angle thereof, and a plurality of blades 32 which extend in the vertical direction, and are capable of moving in the horizontal direction to change an angle thereof are arranged in the air outlet 3. As the angles of the blades 31 and 32 change, the direction of air discharged to the test chamber S changes. A blade actuator 33 is driven to change the angles of the blades 31 and 32 (see FIG. 3). In this thermostat-humidistat chamber 1, the angles of the blades 31 and 32 are automatically optimized as described in detail below.

In the illustrated example, two shelf boards 4 are arranged to be aligned in the vertical direction in the test chamber S, and specimens are placed on the shelf boards 4. The number and the position of the shelf boards 4 can suitably be determined.

Four sensors 5 are arranged respectively on a ceiling surface, and on a bottom surface of the test chamber S to have intervals therebetween, and a single sensor 5 is arranged at the center of the test chamber S (at the center of the shelf board 4 in the illustrated example). The nine sensors 5 in total function as test chamber sensors 5 for measuring the temperature and the humidity at the respective positions in the test chamber S. Based on the measurements of the test chamber sensors 5, distributions of the temperature and the humidity in the test chamber S can be obtained. The number of the test chamber sensors 5 is not limited to nine, and the configuration shown in FIG. 2 is merely an example. The positions of the test chamber sensors 5 can suitably be determined depending on the number of the test chamber sensors 5. However, the test chamber sensors 5 are preferably placed substantially uniformly in the test chamber S to obtain the distributions of the temperature and the humidity in the test chamber S. The number of the test chamber sensors 5 will be described as N in the following description.

In the thermostat-humidistat chamber 1, an air outlet sensor 9 for measuring the temperature and the humidity is arranged near the air outlet 3. The measurements of the air outlet sensor 9 are used for feedback control of the air conditioner 8.

Measurement signals from the air outlet sensor 9 and the test chamber sensors 5 are sent to a controller 6 arranged in a lower portion of the thermostat-humidistat chamber 1. The controller 6 controls the air conditioner 8 based on the measurements of the sensors 5 and 9 in such a manner that the temperature and the humidity in the test chamber S are the predetermined temperature and humidity, respectively.

Figure 3:
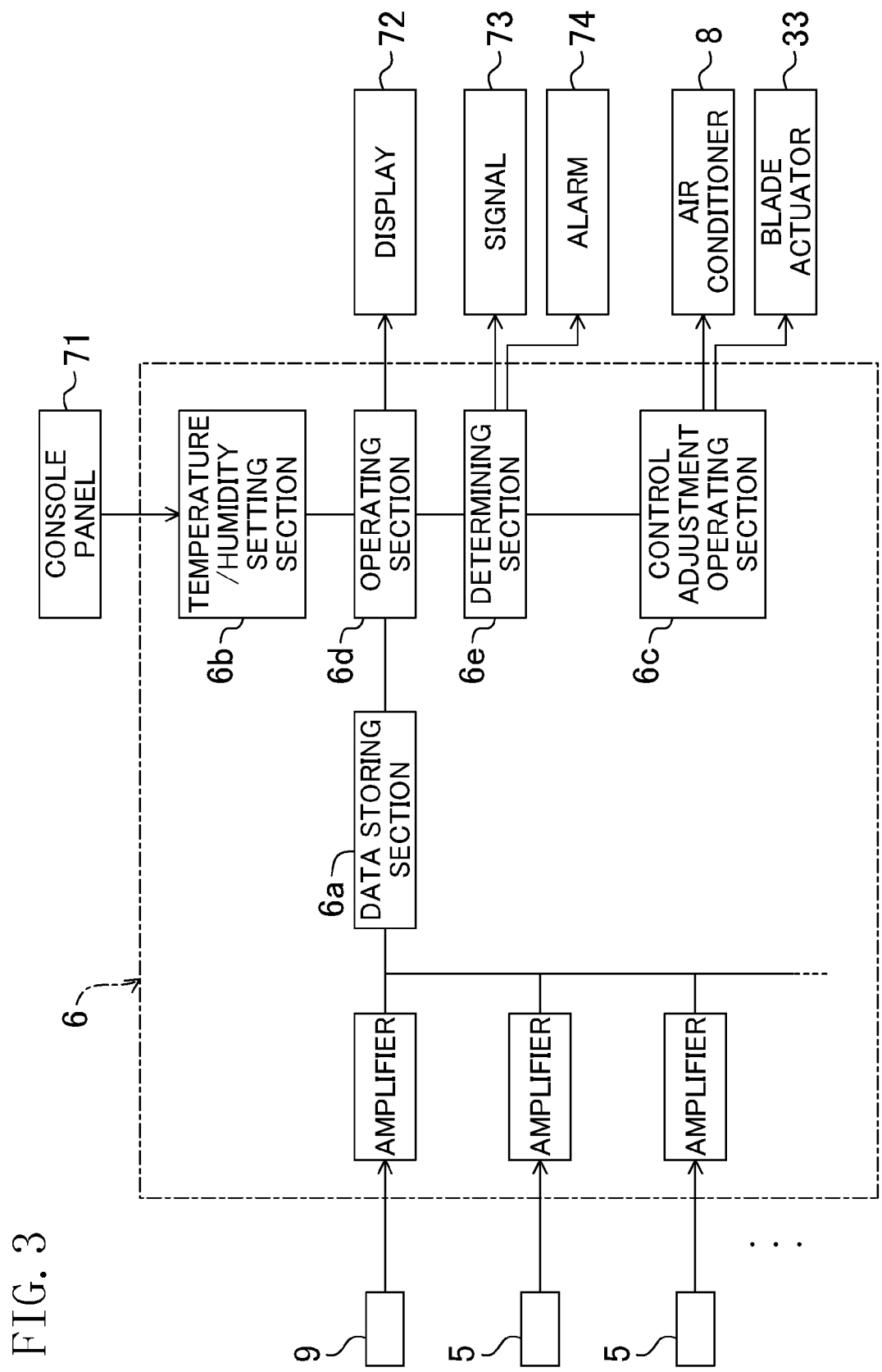
FIG. 3 is a block diagram illustrating an example of a structure in the thermostat-humidistat chamber.

As shown in FIG. 3, the controller 6 includes amplifiers for amplifying the signals sent from the sensors 5 and 9, and a data storing section 6a for storing the signals amplified by the amplifiers.

Although not shown in FIG. 1, the controller 6 further includes a temperature/humidity setting section 6b for setting target values for controlling the temperature and the humidity in the test chamber S based on a signal from a console panel 71 through which an operator sets the target temperature and humidity, and an operating section 6d which receives signals from the temperature/humidity setting section 6b and the data storing section 6a, and carries out various operations for controlling the air conditioner 8 as described below. The results of the operations are shown on a display 72 provided on a door 2 of the thermostat-humidistat chamber 1 as needed (see FIG. 1).

As described in detail below, the controller 6 includes a determining section 6e which determines variations of distributions of the temperature and the humidity in the test chamber S (ranges of distributions). Based on the determination results, a signal 73 (see FIG. 1), or an alarm 74 which give an operator a warning is operated.

The controller 6 further includes a control adjustment operating section 6c which carries out an operation for determining control adjustments of the air conditioner 8 and the blade actuator 33. The air conditioner 8 and the blade actuator 33 are controlled based on the results of the operation of the control adjustment operating section 6c.

Figure 4:
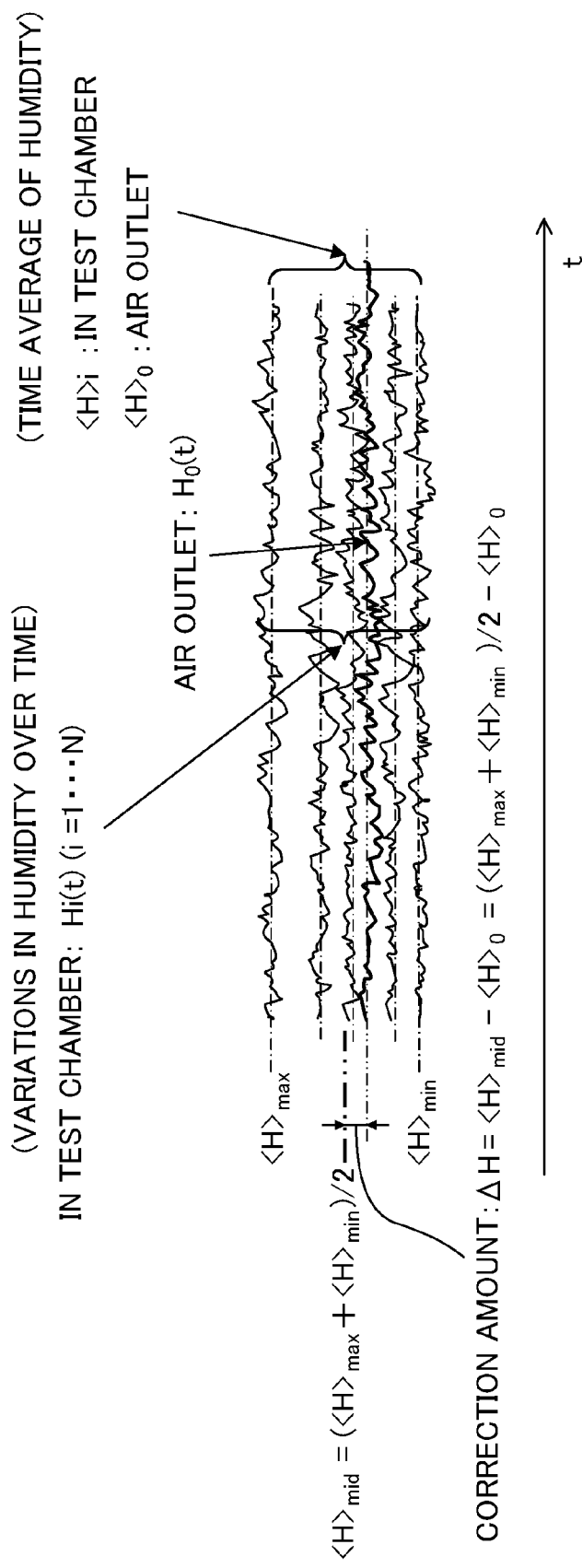
FIG. 4 illustrates a concept of a method for controlling an air conditioner of the thermostat-humidistat chamber.

Referring to FIG. 4, the control of the air conditioner 8 of the thermostat-humidistat chamber 1 will be described below. FIG. 4 shows example humidity measurements of the five test chamber sensors 5, and the single air outlet sensor 9. The number of the test chamber sensors 5 is not particularly limited as described above. Adjustment of the humidity in the test chamber S will be described below as an example of the control of the air conditioner 8. The temperature will be adjusted in the same manner.

Basically, the air conditioner 8 is controlled based on the measurement of the air outlet sensor 9 ($H_0(t)$) arranged near the air outlet 3 in such a manner that the measurement ($H_0(t)$) is a target value ($H_{set}$). Humidity (or temperature) of the conditioned air discharged through the air outlet 3 can change quickly in response to the control of the air conditioner 8 with a small lag, thereby advantageously preventing hunting of the control.

When the air conditioner 8 is controlled based on the measurements obtained near the air outlet 3, the humidity at a different position in the test chamber away from the air outlet 3 may deviate from the target value ($H_{set}$). Thus, the humidity distribution in the test chamber S is not uniform, and may vary as indicated by the measurements of the test chamber sensors 5 ($H_i(t)$ (i=1-5)) shown in FIG. 4.

In this case, it is acceptable that the humidity distribution in the test chamber S varies within the allowable range around the target value ($H_{set}$). However, when the air conditioner 8 is controlled based on the measurements obtained near the air outlet 3 as described above, the range of the humidity distribution in the test chamber S may be shifted to positive, or negative relative to the target value ($H_{set}$). As a result, the humidity measured at a certain different position in the test chamber S may possibly deviate from the allowable range.

In the thermostat-humidistat chamber 1, moving averages of the measurements of the test chamber sensors 5 and the air outlet sensor 9 are calculated (see dot-dashed lines in FIG. 4), and the measurement of the air outlet sensor 9 is corrected based on the calculated moving averages, and the air conditioner 8 is controlled.

Specifically, the moving average ($<H>_i$ (i=1–N)) of the measurements of each of the test chamber sensors 5 (humidity measurements) is calculated from an equation (1).

$$<H>_i = \Sigma_{(j=0-M)} G(j) \cdot H_i(t_j) / \Sigma_{(j=0-M)} G(j) \quad (1)$$

The moving average ($<T>_i$) of temperature measurements is calculated from an equation (2).

$$<T>_i = \Sigma_{(j=0-M)} G(j) \cdot T_i(t_j) / \Sigma_{(j=0-M)} G(j) \quad (2)$$

In the above equations, $t_j = t - j \cdot \Delta t$, and $\tau = M \cdot \Delta t$, where $\Delta t$ is a clock tick, $G(j)$ is a weight function, and $\tau$ is a duration for calculating the average. The weight function $G(j)$ can suitably be determined For example, a simple moving average of the temperature measurements, and a simple moving average of the humidity measurements may be calculated on condition that $G(j)=1$.

Then, a median ($<H>_{mid}$) of the maximum value ($<H>_{max}$) and the minimum value ($<H>_{min}$) of the calculated moving averages is obtained ($<H>_{mid}=(<H>_{max}+<H>_{min})/2$).

A moving average ($<H>_0$) of the measurements of the air outlet sensor 9 is calculated, and the calculated moving average ($<H>_0$) is subtracted from the median ($<H>_{mid}$) to calculate a correction amount $\Delta H$ ($\Delta H=<H>_{mid}-<H>_0$).

Based on the calculated correction amount $\Delta H$, the measurement ($H_0(t)$) of the air outlet sensor 9 is corrected based on the equation $H_0*(t)=H_0(t)+\Delta H$. The measurement of the temperature of the air outlet sensor 9 after the correction is obtained based on the equation $T_0*(t)=T_0(t)+\Delta T$.

Since the correction amount $\Delta H$ (or $\Delta T$) is based on the moving averages, its temporal variation is significantly slower than the temporal variation of the measurement of the air outlet sensor 9. Thus, the corrected value $H_0*(t)$ (or $T_0*(t)$) contains a temporal variation component which is approximately the same as that of the measurement $H_0(t)$ (or $T_0(t)$), and the temporal variation component can quickly change in response to the control of the air conditioner 8 with a small lag.

The corrected value $H_0*(t)$ (or $T_0*(t)$) contains information of a median of the range of distribution of the humidity in the test chamber S.

Thus, the air conditioner 8 is controlled based on the corrected value $H_0*(t)$ in such a manner that the median of the distribution of the humidity in the test chamber S is the target humidity. This can prevent deviation of the range of the distribution from the target humidity, and positive and negative ranges of the distribution of the humidity in the test chamber S relative to the target humidity become equal. Thus, the range of the distribution of the humidity can be prevented from deviating from the allowable range.

As described above, the temporal variation component of the corrected value $H_0*(t)$ can change quickly in response to the control of the air conditioner 8 with a small lag. This can prevent hunting of the control.

In this thermostat-humidistat chamber 1, the air outlet sensor 9 and the test chamber sensors 5 are associated to control the air conditioner 8. Thus, the air conditioner 8 can stably be controlled, and the distributions of the temperature and the humidity in the test chamber S can be prevented from deviating from the allowable ranges.

The temperature and the humidity measured by the air outlet sensor 9 may significantly deviate from the medians of the ranges of the distributions of the temperature and the humidity in the test chamber S in many cases. When the above-described control is repeated in such a case, the control may slow down.

Thus, in this thermostat-humidistat chamber 1, the air conditioner 8 is controlled based on the medians (the moving averages) of the ranges of the distributions of the temperature and the humidity in the test chamber S in the normal operation, thereby allowing stable control of the air conditioner 8, and preventing the temperature and humidity distributions in the test chamber S from deviating from the allowable ranges.

Referring to flowcharts shown in FIGS. 5-10, the control of the air conditioner 8 performed by the controller 6 will be described below.

Figure 5:
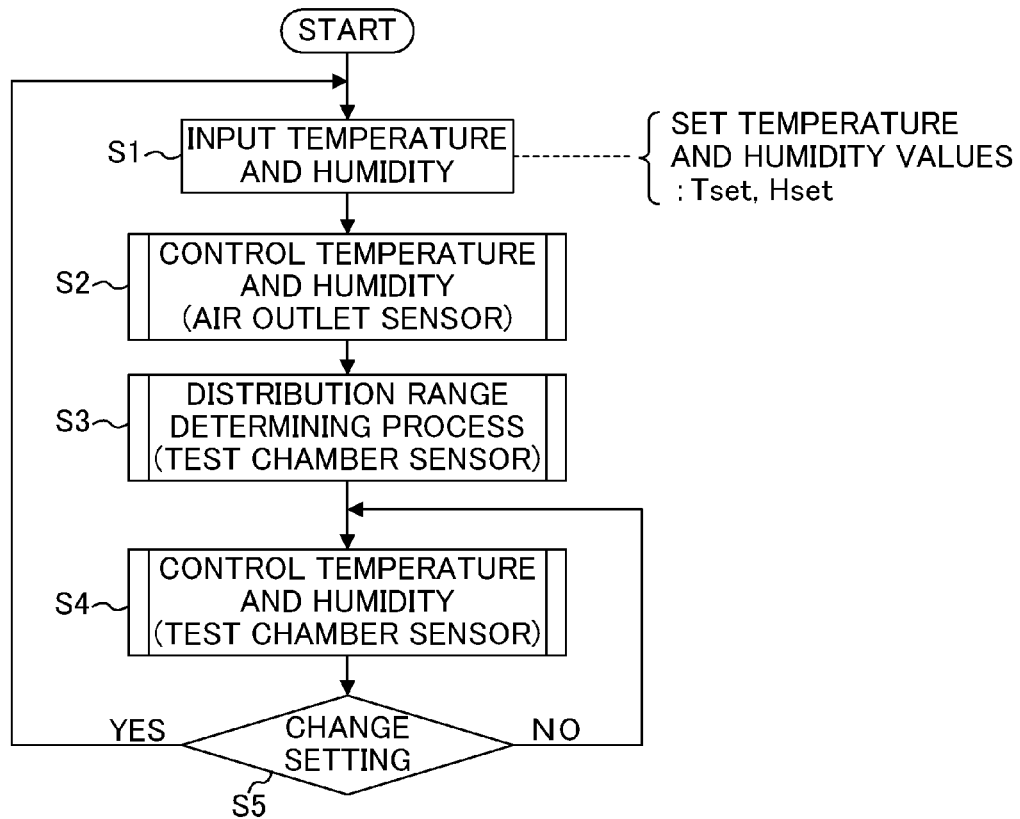
FIG. 5 is a flowchart indicating a general flow of the air conditioner.

FIG. 5 shows a general flow of the temperature and humidity control in the thermostat-humidistat chamber 1. In step S1, a set temperature value and a set humidity value ($T_{set}$, $H_{set}$) as the target values are set based on a signal sent from the console panel 71.

Figure 6:
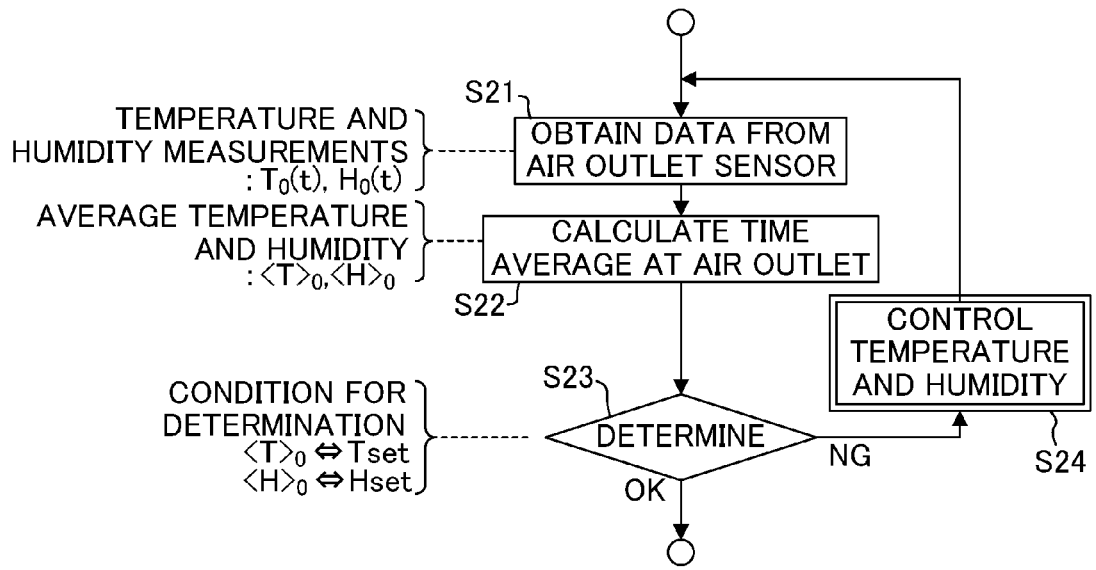
FIG. 6 is a flowchart of temperature/humidity control using an air outlet sensor.

In step S2, the air conditioner 8 is controlled using the measurements of the air outlet sensor 9 only. Specifically, as shown in the flowchart of FIG. 6, temperature measurements and humidity measurements ($T_0(t)$, $H_0(t)$) measured by the air outlet sensor 9 are obtained in step S21, and the moving averages ($<T>_0$, $<H>_0$), i.e., time average values of the temperature and humidity at the air outlet 3, are calculated in step S22. The moving averages ($<T>_0$, $<H>_0$) are calculated based on the equations (1) and (2).

In step S23, the calculated moving averages ($<T>_0$, $<H>_0$) and the set temperature and humidity values ($T_{set}$, $H_{set}$) are compared. When NG is selected (when the moving averages are deviated from the set temperature and humidity values), the flow goes to step S24 to control the air conditioner 8 in such a manner that the moving averages are the set temperature and humidity values, respectively, and then the flow returns to step S21. When OK is selected in step S23 (when the moving averages are approximately the same as the set temperature and humidity values), the flow is terminated.

Back to the flowchart of FIG. 5, in step S3 following step S2, a distribution range determining process is performed. The distribution range determining process is performed to determine whether the range of the distribution of the temperature or the humidity in the test chamber S is as large as, or smaller than the predetermined range. When the range of the distribution is larger than the predetermined range, the angles of the blades 31 and 32 are changed to reduce the range of distribution, an alarm is given to request a check by the operator, or the operation of the thermostat-humidistat chamber 1 is stopped based on a determination that an abnormal event has occurred, depending on how much larger the range of the distribution is than the predetermined range.

Figure 7:
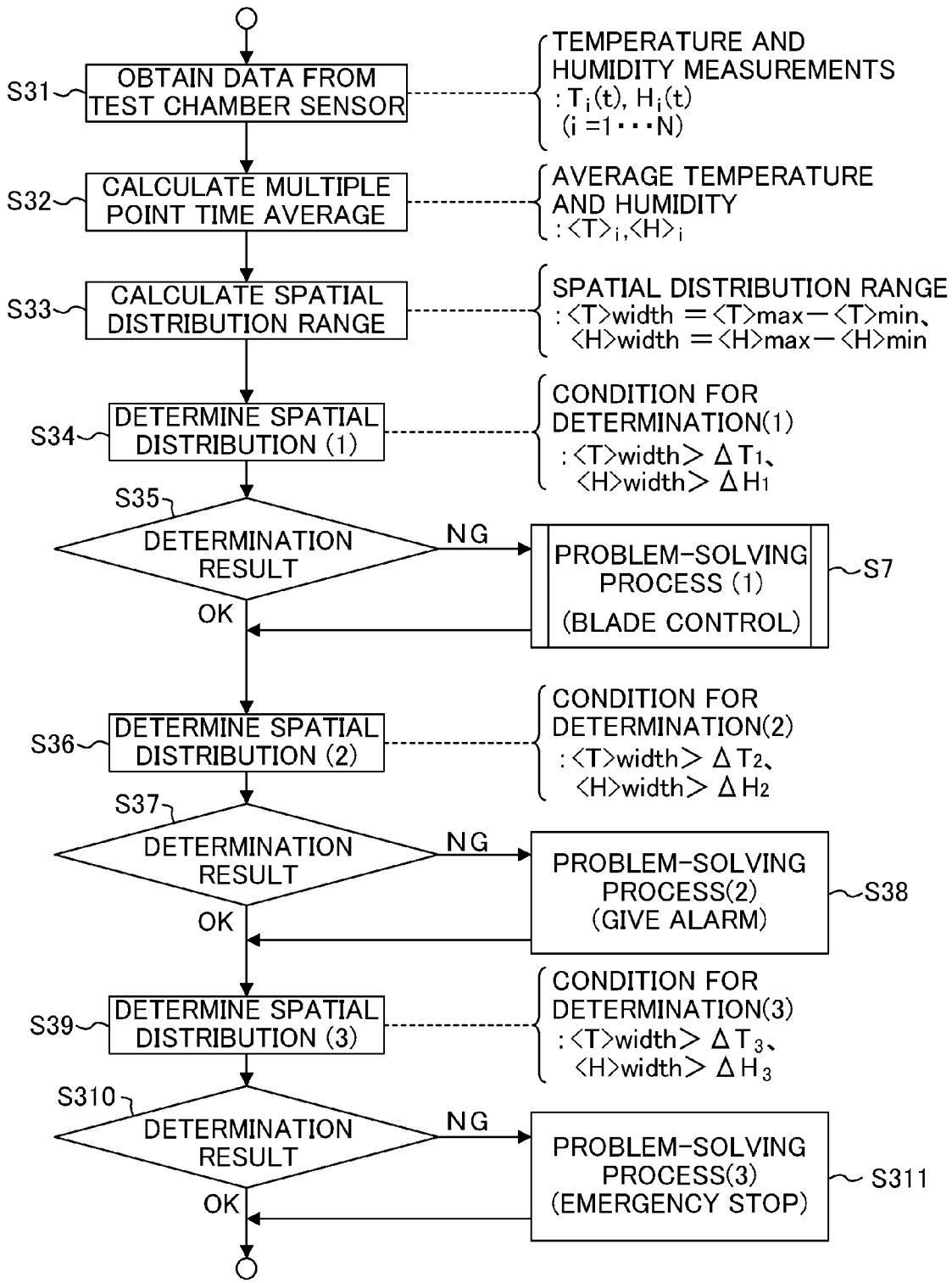
FIG. 7 is a flowchart of a distribution range determining process.

The distribution range determining process is performed along the flow shown in FIG. 7. In step S31, the temperature measurements and the humidity measurements ($T_i(t)$, $H_i(t)$ (i=1–N)) of the test chamber sensors 5 are obtained, and moving averages ($<T>_i$, $<H>_i$), i.e., time average values of the temperature and humidity, are calculated in step S32. The moving averages ($<T>_i$, $<H>_i$) are also calculated based on the equations (1) and (2).

In step S33, a spatial distribution range ($<T>_{width}$, $<H>_{width}$) is calculated. The multiple point distribution range is a difference between the maximum value ($<T>_{max}$, $<H>_{max}$) and the minimum value ($<T>_{min}$, $<H>_{min}$) of the moving averages ($<T>_i$, $<H>_i$) of the measurements of the plurality of test chamber sensors ($<T>_{width}=<T>_{max}=<T>_{min}$, $<H>_{width}=<H>_{max}-<H>_{min}$).

In step S34, whether the spatial distribution range ($<T>_{width}$, $<H>_{width}$) is wider than the predetermined range ($\Delta T1$, $\Delta H1$) is determined When the multiple point distribution range is wider than the predetermined range, i.e., $<T>_{width}>\Delta T1$, or $<H>_{width}>\Delta H1$, and NG is selected in step S35, the flow goes to step S7 to perform control of the blades as a problem-solving process (1). When the multiple point distribution range is as wide as, or narrower than the predetermined range, i.e., $<T>_{width}\leq\Delta T1$, or $<H>_{width}\leq\Delta H1$, and OK is selected in step S35, the flow proceeds to step S36.

Figure 9:
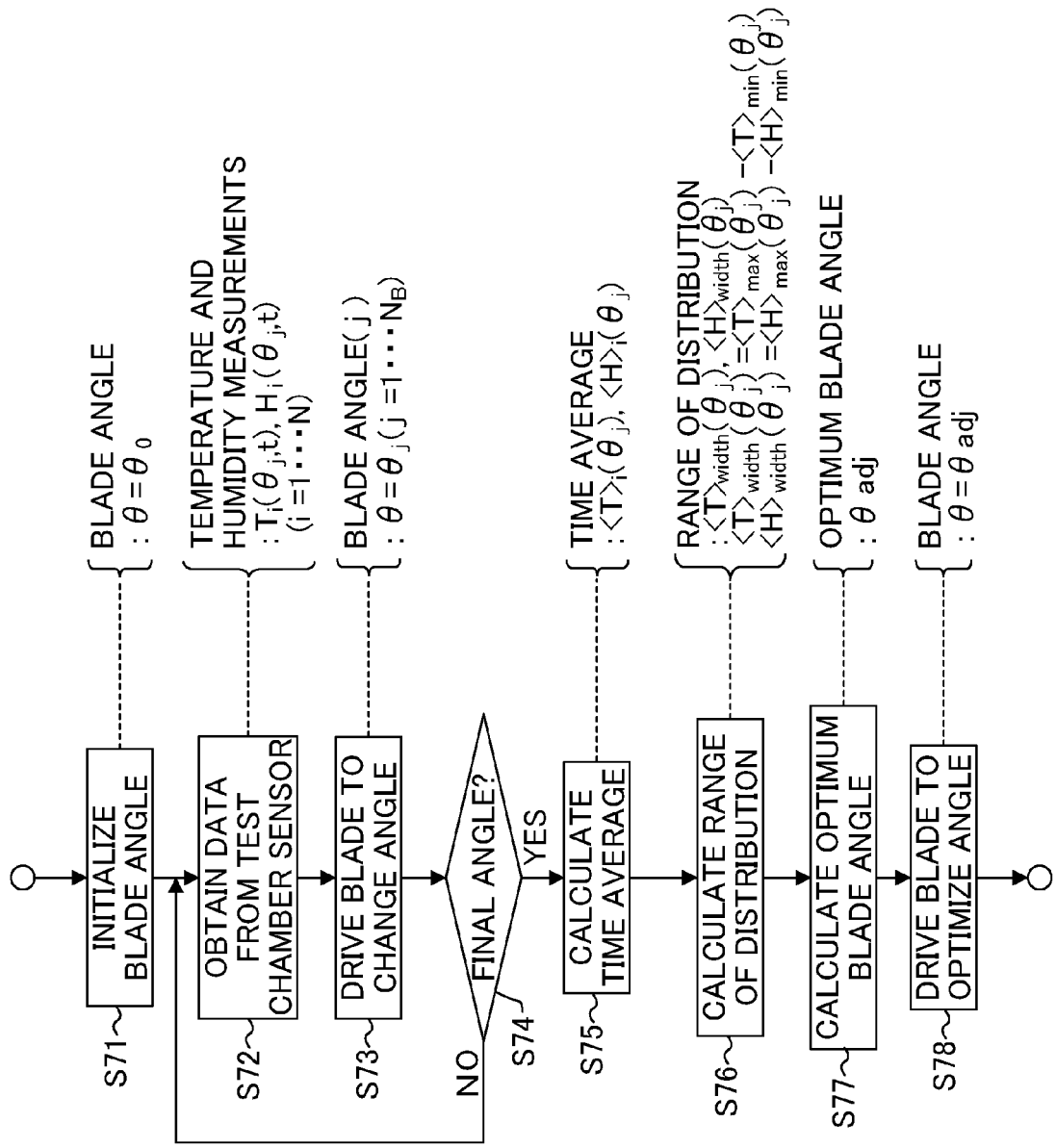
FIG. 9 is a flowchart of blade control.

The control of the blades in step S7 is carried out along the flowchart shown in FIG. 9. Specifically, the control of the blades is performed by setting the angles of the blades at which the ranges of the distributions of the temperature and the humidity in the test chamber S are reduced as much as possible. The blades are controlled by measuring the temperature and humidity distributions by the test chamber sensors 5, while the angles of the blades 31 and 32 are actually changed by driving the blade actuator 33.

The angles of the blades 31 and 32 may be changed one by one. However, the number of combinations becomes enormous depending on the number of the blades 31 and 32 and the range of their angles. Thus, some angle patterns each defining the combination of the angles of the blades 31 and 32 may be determined in advance, and the angles of the blades may be changed by changing the angle pattern.

In the flow shown in FIG. 9, the angles of the blades are initialized in step S71 ($\theta=\theta_0$), and the measurements of the test chamber sensors 5 (temperature and humidity) are obtained in step S72 ($T_i(\theta_j, t)$, $H_i(\theta_j, t)$, where i represents the test chamber sensor 5 (i=1−N), and $\theta_j$ represents the angle of the blade (j=0−$N_B$)).

In step S73, the blade actuator 33 is driven to change the angles of the blades, and whether the angles of the blades are the final angles (whether $\theta=\theta_{NB}$ or not) is determined in step S74. When NO is selected in step S74, the flow returns to step S72, and the measurements of the test chamber sensors 5 (temperature and humidity) are obtained again as described above. When YES is selected in step S74, the flow proceeds to step S75. Thus, in step S72-S74, the spatial distributions of the temperature and the humidity in the test chamber S are obtained while changing the angles of the blades 31 and 32.

In step S75, the moving averages ($<T>_i(\theta_j)$, $<H>_i(\theta_j)$) are obtained from the obtained measurements, and, the ranges of the distributions of the temperature and the humidity at every blade angle $\theta_j$ are calculated in the step S76 ($<T>_{width}(\theta_j)$, $<H>_{width}(\theta_j)$). Specifically, the calculation is performed based on the equations $<T>_{width}(\theta_j)=<T>_{max}(\theta_j)-<T>_{min}(\theta_j)$, and $<H>_{width}(\theta_j)=<H>_{max}(\theta_j)-<H>_{min}(\theta_j)$.

Based on the calculation results in step S76, the blade angle $\theta_j$ at which the ranges of the distributions ($<T>_{width}(\theta_j)$, $<H>_{width}(\theta_j)$) are reduced as much as possible is set as an optimum blade angle $\theta_{adj}$ in step S77. In step S78, the blade actuator 33 is driven to adjust the angles of the blades 31 and 32 to the optimum blade angle $\theta_{adj}$. In this way, the ranges of the distributions of the temperature and the humidity in the test chamber S can be reduced.

Back to the flow shown in FIG. 7, the multiple point distribution range ($<T>_{width}$, $<H>_{width}$) is calculated again, and whether the multiple point distribution range ($<T>_{width}$, $<H>_{width}$) is wider than the predetermined range ($\Delta T2$, $\Delta H2$) is determined in step S36. $\Delta T2$ is smaller than $\Delta T1$, and $\Delta H2$ is smaller than $\Delta H1$. When the multiple point distribution range is wider than the predetermined range ($<T>_{width}>\Delta T2$, or $<H>_{width}>\Delta H2$), the flow proceeds from step S37 to step S38, and a problem-solving process (2) is performed, i.e., the alarm 74 is operated, and a warning lamp of the signal 73 is lit. Specifically, when the ranges of the distributions of the temperature and the humidity in the test chamber S are wider than the predetermined ranges ($\Delta T2$, $\Delta H2$) even after the ranges of the distributions of the temperature and the humidity in the test chamber S are reduced by controlling the angles of the blades, it is considered that some troubles have occurred. This state is regarded as a moderate failure state. Then, the alarm 74 is operated, and the signal 73 is lit to give an alert to the operator, and to urge the operator to perform a check. When the multiple point distribution range is as wide as, or is narrower than the predetermined range ($<T>_{width}\leq\Delta T2$, and $<H>_{width}\leq\Delta H2$), the flow proceeds from step S37 to step S39. When the check by the operator is finished in step S38, the flow proceeds to step S39.

In step S39, the multiple point distribution range ($<T>_{width}$, $<H>_{width}$) is calculated again, and whether the multiple point distribution range ($<T>_{width}$, $<H>_{width}$) is wider than the predetermined range ($\Delta T3$, $\Delta H3$) is determined. $\Delta T3$ is larger than $\Delta T2$, and $\Delta H3$ is larger than $\Delta H2$. When the multiple point distribution range is wider than the predetermined range ($<T>_{width}>\Delta T3$, or $<H>_{width}>\Delta H3$), the flow proceeds from step S310 to step S311, and a problem-solving process (3) is performed, i.e., the thermostat-humidistat chamber 1 is stopped. Specifically, when the ranges of the distributions of the temperature and the humidity in the test chamber S are significantly wide even after the ranges of the distributions of the temperature and the humidity in the test chamber S are reduced by controlling the angles of the blades, and the check by the operator is finished, it is considered that some troubles have occurred. This state is regarded as a severe failure state, and the thermostat-humidistat chamber 1 is stopped. When the multiple point distribution range is as wide as, or narrower than the predetermined range ($<T>_{width}\leq\Delta T3$, and $<H>_{width}\leq\Delta H3$), the flow is terminated.

In the present embodiment, the three processes (the blade control, the alarm, and emergency stop) are carried out as pass/fail processes. Any two of the three processes may be carried out, or any one of the three processes may be carried out. An additional process may be added to perform four or more pass/fail processes.

Figure 8:
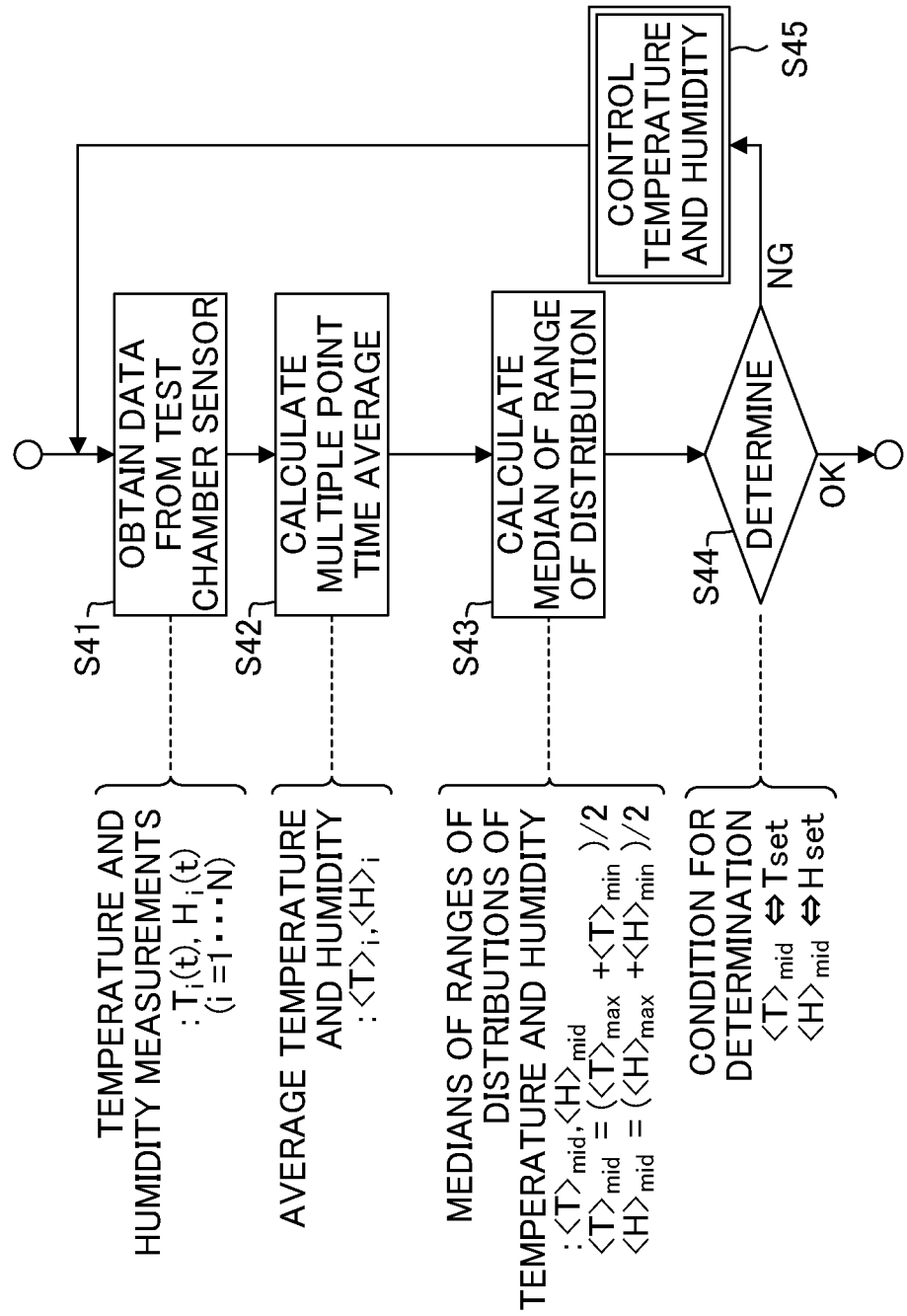
FIG. 8 is a flowchart of temperature/humidity control using test chamber sensors.

Back to step S4 in the flow shown in FIG. 5, the air conditioner 8 is controlled by using only the measurements of the test chamber sensors 5. Specifically, as shown in the flow of FIG. 8, the temperature measurements and the humidity measurements ($T_i(t)$, $H_i(t)$ (i=0−N)) of the test chamber sensors 5 are obtained in step S41, and then the moving averages ($<T>_i$, $<H>_i$), i.e., time average values of the temperature and humidity, of the measurements are calculated in step S42. The moving averages ($<T>_i$, $<H>_i$) are calculated based on the equations (1) and (2).

In step S43, a median of the range of the distribution ($<T>_{mid}$, $<H>_{mid}$) is calculated. Specifically, based on the maximum value ($<T>_{max}$, $<H>_{max}$) and the minimum value ($<T>_{min}$, $<H>_{min}$) of the calculated moving averages, the median of the range of the distribution is calculated based on the equations $<T>_{mid}=(<T>_{max}+<T>_{min})/2$, and $<H>_{min}=(<H>_{max}+<H>_{min})/2$.

In step S44, the medians of the ranges of the temperature and humidity distributions ($<T>_{mid}$, $<H>_{mid}$) and the set temperature and humidity values ($T_{set}$, $H_{set}$) are compared, respectively. When NG is selected (when the medians of the ranges of the distributions are deviated from the set temperature and humidity values), the flow goes to step S45 to control the air conditioner 8 in such a manner that the medians are the set temperature and humidity values, and then the flow returns to step S41. When OK is selected in step S44 (when the medians of the ranges of the distributions are substantially the same as the set temperature and humidity values), the flow is terminated.

Back to the flow shown in FIG. 5, whether the set temperature and humidity values are changed or not is determined in step S5. The flow returns to step S1 when the values are changed (YES is selected), or the flow returns to step S4 when the values are not changed (NO is selected). Thus, when the set temperature and humidity values are changed, steps S1-S4 are repeated, and the air conditioner 8 is controlled based on the measurements of the air outlet sensor 9 in such a manner that the temperature and the humidity are the changed set temperature and humidity values, and the angles of the blades 31 and 32 are controlled in such a manner that the ranges of the distributions of the temperature and the humidity are reduced as much as possible. When the set temperature and humidity values are not changed, the air conditioner 8 is controlled based on the measurements of the test chamber sensors 5.

Thus, in this thermostat-humidistat chamber 1, the air outlet sensor 9 and the test chamber sensors 5 are associated to control the air conditioner 8. Specifically, the air conditioner 8 is controlled in such a manner that the medians of the ranges of the distributions of the temperature and the humidity in the test chamber S are the target temperature and humidity, respectively. This can prevent the ranges of the distributions of the temperature and the humidity from deviating from the target temperature and humidity, thereby reducing the deviation of the ranges of the temperature and humidity distributions in the test chamber S from the allowable ranges.

In this case, the air conditioner 8 can stably be controlled when the air conditioner 8 is controlled based on the moving averages of the measurements in the test chamber S.

In particular, in initializing or changing the target temperature and humidity values, the control for changing the angles of the blades 31 and 32 is carried out to reduce the ranges of the distributions of the temperature and the humidity as much as possible. This can reliably prevent the deviation of the ranges of the temperature and humidity distributions in the test chamber S from the allowable ranges.

In this thermostat-humidistat chamber 1, the air conditioner 8 is controlled based on the moving averages during the normal operation. Since the moving averages merely vary slowly, the control may become unstable during a transient period in which the target values are changed. In the control during the transient period of the air conditioner 8 for initializing or changing the target values, the air conditioner 8 is feedback-controlled using the moving average of the measurements of the air outlet sensor 9, thereby keeping the control of the air conditioner 8 stable, and immediately changing the temperature and the humidity in the test chamber S to be close to the target temperature and humidity.

(Second Embodiment)

Figure 10:
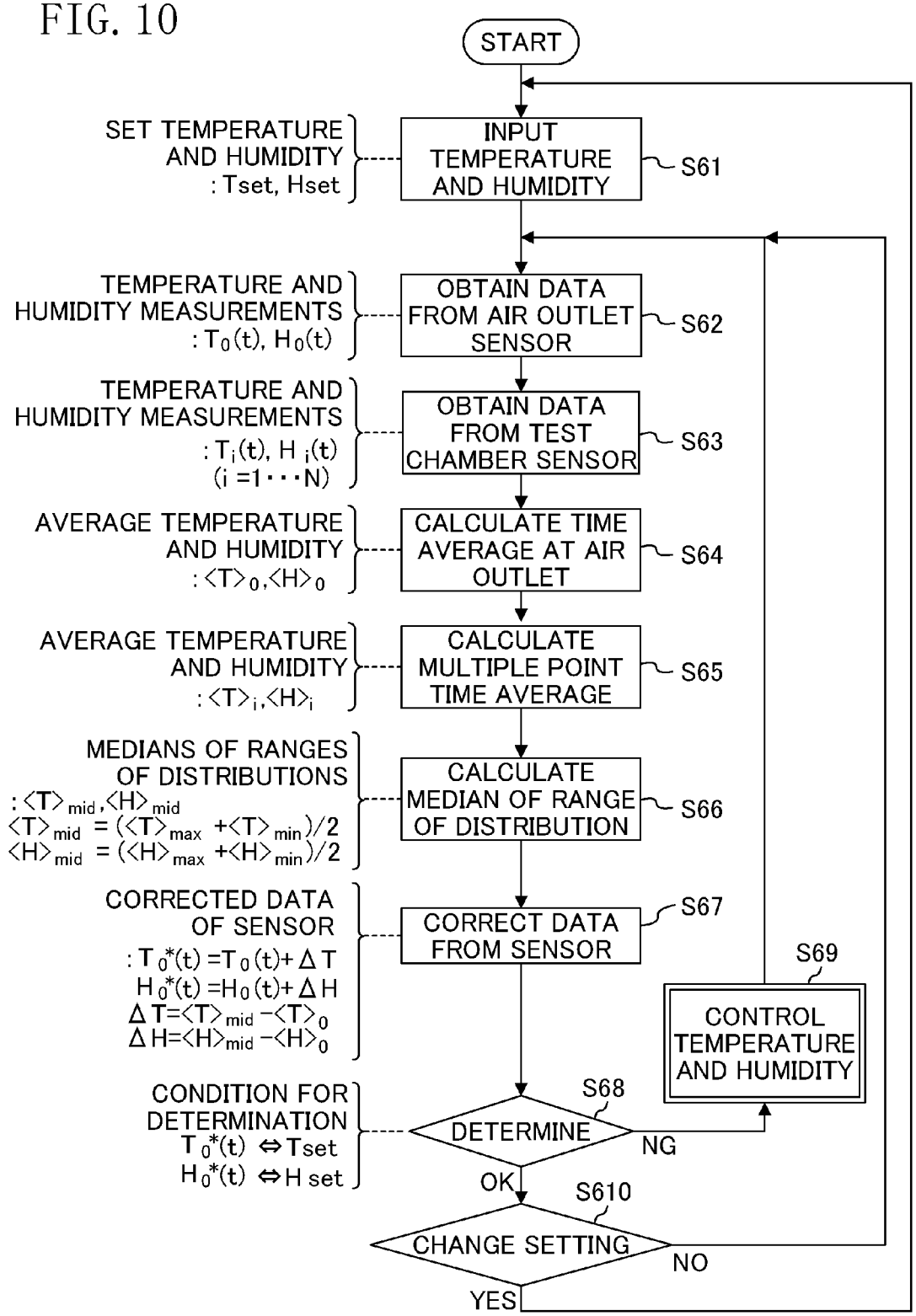
FIG. 10 is a flowchart indicating a control flow of an air conditioner of a second example embodiment.

FIG. 10 shows a flow for controlling the air conditioner 8 according to a second embodiment. In step S61, set temperature and humidity values ($T_{set}$, $H_{set}$) as the target values are set based on a signal from the console panel 71.

In step S62, the temperature measurements and the humidity measurements ($T_0(t)$, $H_0(t)$) of the air outlet sensor 9 are obtained, and the temperature measurements and the humidity measurements ($T_i(t)$, $H_i(t)$ (i=1–N)) of the test chamber sensors 5 are obtained in step S63.

In step S64, moving averages of the temperature measurements and the humidity measurements of the air outlet sensor 9 ($<T>_0$, $<H>_0$) are calculated, and moving averages of the temperature measurements and the humidity measurements of the test chamber sensors 5 ($<T>_i$, $<H>_i$) are calculated in step S65. In step S66, medians of the ranges of the distributions of the temperature and humidity measurements ($<T>_{mid}$, $<H>_{mid}$) in the test chamber sensors 5 (moving averages) are calculated.

In step S67, based on the medians of the ranges of the distributions ($<T>_{mid}$, $<H>_{mid}$), and the moving averages of the measurements of the air outlet sensor 9 ($<T>_c$), $<H>_0$), a correction amount for correcting the temperature, and a correction amount for correcting the humidity ($\Delta T$, $\Delta H$) are calculated ($\Delta T=<T>_{mid}-<T>_0$, $\Delta H=<H>_{mid}-<H>_0$). Then, the measurements of the air outlet sensor 9 are corrected using the calculated correction amounts. Specifically, the correction is performed based on the equations $T_0^*(t)=T_0(t)+\Delta T$, and $H_0^*(t)=H_0(t)+\Delta H$.

In step S68, the corrected temperature measurement $T_0^*(t)$ of the air outlet sensor 9 is compared with the target temperature value $T_{set}$, and the corrected humidity measurement $H_0^*(t)$ of the air outlet sensor 9 is compared with the target humidity value $H_{set}$. When NG is selected (when the corrected temperature measurement $T_0^*(t)$ or the corrected humidity measurement $H_0^*(t)$ is deviated from the target temperature or humidity value $T_{set}$, $H_{set}$), the flow proceeds to step S69 to control the air conditioner 8 to remove the deviation, and then the flow returns to step S62. When OK is selected in step S68 (when the corrected temperature measurement $T_0^*(t)$ and the corrected humidity measurement $H_0^*(t)$ are substantially the same as the target temperature and humidity values $T_{set}$, $H_{set}$), the flow proceeds to step S610 to determine whether the set temperature and humidity values are changed or not. When the values are changed (YES is selected), the flow returns to step S61. When the values are not changed (NO is selected), the flow returns to step S62.

In the second embodiment, the measurements of the air outlet sensor 9 are corrected based on the medians of the ranges of the distributions of the temperature and the humidity in the test chamber S, thereby controlling the air conditioner 8 in such a manner that the medians of the ranges of the distributions of the temperature and the humidity in the test chamber S are the target temperature and humidity values, respectively. This can prevent the deviation of the ranges of the distributions of the temperature and the humidity from the target temperature and humidity values, and can reduce the deviation of the ranges of the distributions of the temperature and the humidity in the test chamber S from the allowable ranges.

The correction amount is determined based on the moving averages of the measurements of the sensors 5 and 9. Thus, the corrected measurement of the air outlet sensor 9 ($T_0^*(t)$, RAW has a temporal variation component which is approximately the same as a temporal variation component of the measurement ($T_0(t)$, $H_0(t)$) of the air outlet sensor 9 arranged near the air outlet 3. The corrected measurement can change quickly in response to the control of the air conditioner 8 with a small lag, thereby preventing hunting of the control.

In each of the above embodiments, the air outlet sensor 9 is arranged near the air outlet 3. However, the sensor 9 may be arranged near the air inlet, for example, to perform the control in the same manner as described above.

In each of the above embodiments, the plurality of test chamber sensors 5 are arranged in the test chamber S. However, for example, the number of the test chamber sensors 5 in the test chamber S may be reduced to one. In this case, the median of the range of the distribution etc. may be calculated on condition that the maximum value ($<T>_{max}$, $<H>_{max}$) and the minimum value ($<T>_{min}$, $<H>_{min}$) are the same ($<T>_{max}=<T>_{min}$, $<H>_{max}=<H>_{min}$), i.e., are the same as the moving average of the measurements of the test chamber sensor 5 of the above embodiments.

In the above embodiments, the method for controlling the air conditioner has been described by way of an example of the thermostat-humidistat chamber 1. However, the control method may be applied to environment testers (environment test chambers), such as thermostat chambers which stably keep the temperature in the test chamber S within the predetermined range. The disclosed air conditioner and method for controlling the air conditioner are effective in keeping the spatial distributions of the temperature and the humidity in the closed space within the allowable ranges, and are applicable, not only to the environmental testers, but also to a wide variety of apparatuses, such as environmental testers, comfort air conditioners for houses, stores, and various facilities, industrial air conditioners for plants, warehouses, and various facilities, refrigerating apparatuses such as refrigerators, refrigerated containers, etc. Depending on the apparatus to which the disclosed technology is applied, the air inlet sensor and the test chamber sensors described above may be replaced with a sensor which measures the physical quantity from a remote position.

Industrial Applicability

As described above, the disclosed technology allows stable control of the air conditioner, and keeps the range of variations in spatial distribution of the physical quantity, such as temperature and humidity, in the closed space within the allowable range. Thus, the disclosed technology is applicable to a wide variety of apparatuses, such as environmental testers, comfort air conditioners for houses, stores, and various facilities, industrial air conditioners for plants, warehouses, and various facilities, refrigeration apparatuses such as refrigerators, refrigerated containers, etc.

DESCRIPTION OF REFERENCE CHARACTERS

3 Air outlet
31, 32 Blade
5 Test chamber sensor (sensor)
6 Controller
6b Temperature/humidity setting section (setting section)
6c Control adjustment operating section (controller)
6d Operating section
8 Air conditioner
9 Air outlet sensor
S Test chamber (closed space)

The invention claimed is:

1. A method for controlling an air conditioner which conditions air sucked from closed space through an air inlet, and then discharges the conditioned air to the closed space through an air outlet, thereby controlling a state in the closed space to a predetermined target state, the method comprising:
setting a target value for controlling a physical quantity representing the state of the closed space;
during a moving predetermined time period in which the air conditioner is operating, first measuring the physical quantity of the air discharged through the air outlet, or sucked through the air inlet over time;
during the time period second measuring the physical quantity over time at least one position in the closed space which is not near the air outlet and the air inlet;
during the time period first calculating a moving average of measurements of the physical quantity obtained at one of the air outlet and the air inlet, in the first measuring;
during the time period second calculating a moving average of measurements of the physical quantity in the closed space obtained in the second measuring;
calculating a correction amount by subtracting the moving average of the measurements of the physical quantity obtained at the one of the air outlet and the air inlet during the time period from the moving average of the measurements of the physical quantity obtained in the closed space;
adding the calculated correction amount to the physical quantity measured in the first measuring to calculate a physical quantity for control, and
controlling operation of the air conditioner during the time period in such a manner that the physical quantity for control is the target value.

2. The method of claim 1, wherein the physical quantity is humidity (H) and wherein the moving average (<H>i) is calculated from the following formula:

$$<H>_i = \Sigma_{(j=0-M)} G(j) \cdot H_i(t_j) / \Sigma_{(j=0-M)} G(j),$$

wherein t is time, $t_j = t - j \cdot \Delta t$, $\tau = M \cdot \Delta t$ where $\Delta t$ is clock tick, $G(j)$ is a weight function, and $\tau$ is a duration for calculating the average.

3. The method of claim 1, wherein the physical quantity is temperature (T) and wherein the moving average (<T>i) is calculated from the following formula:

$$<T>_i = \Sigma_{(j=0-M)} G(j) \cdot T_i(t_j) / \Sigma_{(j=0-M)} G(j),$$

wherein t is time, $t_j = t - j \cdot \Delta t$, $\tau = M \cdot \Delta t$ where $\Delta t$ is clock tick, $G(j)$ is a weight function, and $\tau$ is a duration for calculating the average.

4. An air conditioner comprising:
an air conditioning part which conditions air sucked from closed space through an air inlet, and discharges the conditioned air to the closed space through an air outlet;
a first sensor for measuring a physical quantity at one of the air outlet and the air inlet;
a second sensor adapted to measure the physical quantity at different positions in the closed space during a moving predetermined time period in which the air conditioner is operating; and
a controller for controlling the air conditioning part based on measurements of the sensor in such a manner that a state in the closed space is a predetermined target state,
wherein the controller includes:
a setting section for setting a target value for controlling the physical quantity based on an input signal;
a first calculating section for calculating a moving average of the measurements of the physical quantity measured at the one of the air outlet and the air inlet;
a second calculating section for calculating a moving average of the measurements of the physical quantity measured at each of the different positions during the time period;
a correction amount calculating section for calculating a correction amount by subtracting the moving average of the measurements of the physical quantity calculated by the first calculating section from the moving average of the measurements of the physical quantity calculated by the second calculating section;
a physical amount correcting section for calculating a physical quantity for control by adding the correction amount calculated by the correction amount calculating section to the physical quantity measured by the first sensor; and
a controlling section for controlling operation of the air conditioning part during the time period in such a manner that the physical quantity for control calculated by the physical amount correcting section is the target value.

5. The air conditioner of claim 4, wherein the physical quantity is humidity (H) and wherein the moving average (<H>i) is calculated from the following formula:

$$<H>_i = \Sigma_{(j=0-M)} G(j) \cdot H_i(t_j) / \Sigma_{(j=0-M)} G(j),$$

wherein t is time, $t_j = t - j \cdot t$, $\tau = M \cdot \Delta t$ where $\Delta t$ is clock tick, $G(j)$ is a weight function, and $\tau$ is a duration for calculating the average.

6. The air conditioner of claim 4, wherein the physical quantity is temperature (T) and wherein the moving average (<T>i) is calculated from the following formula:

$$<T>_i = \Sigma_{(j=0-M)} G(j) \cdot T_i(t_j) / \Sigma_{(j=0-M)} G(j),$$

wherein t is time, $t_j = t - j \cdot \Delta t$, $\tau = M \cdot \Delta t$ where $\Delta t$ is clock tick, $G(j)$ is a weight function, and $\tau$ is a duration for calculating the average.

7. An environmental tester comprising:
a test chamber in which a specimen is placed;
an air conditioner which conditions air sucked from the test chamber through an air inlet, and discharges the conditioned air to the test chamber through an air outlet;
a first sensor for measuring a physical quantity at one of the air outlet and the air inlet;

a second sensor adapted to measure a physical quantity at different positions in the test chamber during a moving predetermined time period in which the air conditioner is operating; and a controller for controlling the air conditioner based on measurements of the sensor in such a manner that a state in the test chamber is a predetermined target state, wherein the controller includes:

a setting section for setting a target value for controlling the physical quantity based on an input signal;

a first calculating section for calculating a moving average of the measurements of the physical quantity measured at the one of the air outlet and the air inlet;

a second calculating section for calculating a moving average of measurements of the physical quantity measured at each of the different positions during the time period;

a correction amount calculating section for calculating a correction amount by subtracting the moving average of the measurements of the physical quantity calculated by the first calculating section from the moving average of the measurements of the physical quantity calculated by the second calculating section;

a physical amount correcting section for calculating a physical quantity for control by adding the correction amount calculated by the correction amount calculating section to the physical quantity measured by the first sensor; and a controlling section for controlling operation of the air conditioner during the time period in such a manner that the physical quantity for control calculated by the physical amount correcting section is the target value.

8. The environmental tester of claim 7, wherein the physical quantity is humidity (H) and wherein the moving average ($<H>$i) is calculated from the following formula:

$$<H>_i = \Sigma_{(j=0-M)} G(j) \cdot H_i(t_j) / \Sigma_{(j=0-M)} G(j),$$

wherein t is time, $t_j = t - j \cdot \Delta t$, $\tau = M \cdot \Delta t$ where $\Delta t$ is clock tick, $G(j)$ is a weight function, and $\tau$ is a duration for calculating the average.

9. The environmental tester of claim 7, wherein the physical quantity is temperature (T) and wherein the moving average ($<T>$i) is calculated from the following formula:

$$<T>_i = \Sigma_{(j=0-M)} G(j) \cdot T_i(t_j) / \Sigma_{(j=0-M)} G(j)$$

wherein t is time, $t_j = t - j \cdot \Delta t$, $\tau = M \cdot \Delta t$ where $\Delta t$ is clock tick, $G(j)$ is a weight function, and $\tau$ is a duration for calculating the average.

* * * * *